United States Patent [19]

Reyes, Jr.

[11] Patent Number: 4,557,260
[45] Date of Patent: Dec. 10, 1985

[54] PELVIC SUPPORT FOR MEDICAL PROCEDURES

[76] Inventor: Pedro M. Reyes, Jr., 1467 Montezuma, West Covina, Calif. 91791

[21] Appl. No.: 516,380

[22] Filed: Jul. 22, 1983

[51] Int. Cl.⁴ .................. A61B 19/00; A61B 17/42
[52] U.S. Cl. .................................. 128/134; 5/431; 269/328
[58] Field of Search ............. 128/1 R, 361, 132–134, 128/303 R; 604/356; 269/328; 5/431, 436, 443

[56] References Cited

U.S. PATENT DOCUMENTS 3,532,336 10/1970 Baker .................. 604/356 X
4,080,968 3/1978 Nielsen ................. 604/356

Primary Examiner—Dalton L. Truluck
Attorney, Agent, or Firm—Boniard I. Brown

[57] ABSTRACT

A hip lifter or pelvic support for supporting and positioning the pelvic portion of a patient in an elevated position for examination and other medical procedures. The support is characterized by a forward inclined ramp-like portion which facilitates placement of the support under a prone patient and supports a patient's lower back, an elevated concave platform surface extending rearwardly from the upper edge of the ramp for receiving and supporting the patient's buttocks, and a central rearwardly facing indentation or recess at the rear end of the support which provides clearance for a medical instrument, such as a speculum, required in the examination or other medical procedure performed on the patient.

10 Claims, 5 Drawing Figures

U.S. Patent  Dec. 10, 1985  4,557,260
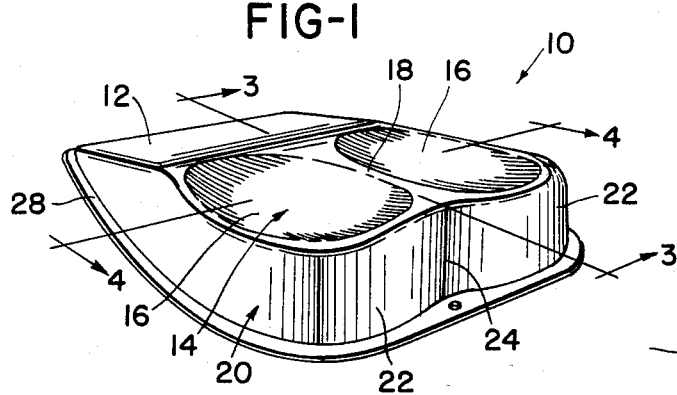
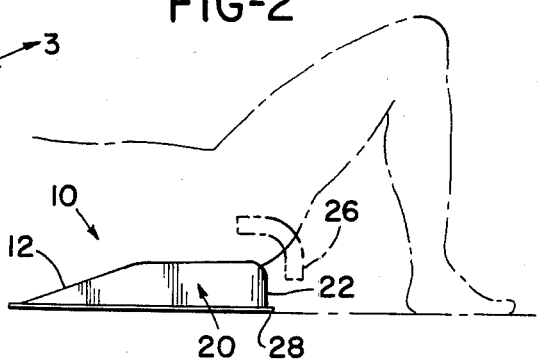
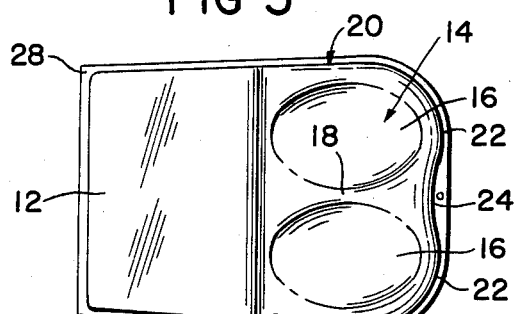
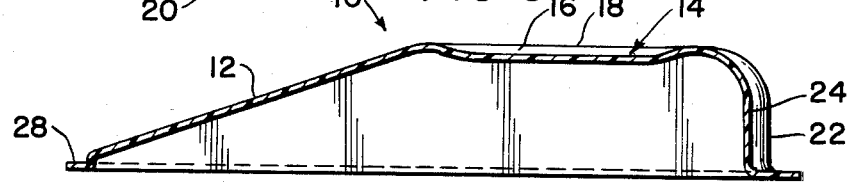
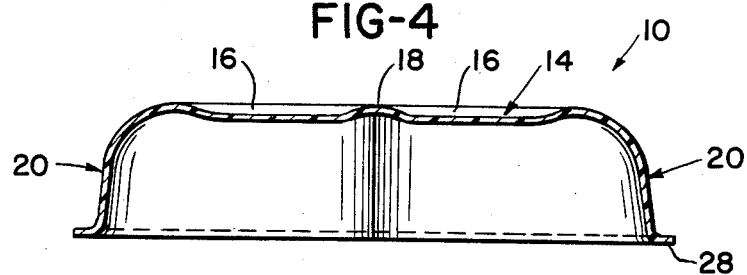

PELVIC SUPPORT FOR MEDICAL PROCEDURES

BACKGROUND OF THE INVENTION

1. Field of the Invention

This invention relates generally to medical aids and more particularly, to a hip lifter or pelvic support for supporting and positioning the pelvic portion of a patient in an elevated position for examination or other medical procedures.

2. Prior Art

Gynecological examination of female patients and other gynecological procedures not requiring an operating room environment are performed in a variety of medical settings. Examples of these settings are hospital emergency rooms, hospital wards, labor and delivery rooms, doctor's offices, and radiological facilities. Most, if not all, of these settings lack access, or at least immediate convenient access, to the patient supporting and lifting devices which are either essential to or extremely desirable for performing many gynecological examinations and other gynecological procedures.

In this regard, for example, gynecological or pelvic examination of a female patient is most easily and effectively performed with the patient in a prone position, with her pelvic portion supported in an elevated inclined attitude, and with sufficient clearance between the patient's pelvic region and the patient's support to permit unrestricted use of a speculum or other medical instrument required in the procedure. A regular gynecological examination facility is equipped with a gynecological examination table, commonly referred to as a GYN table, which is designed to support the patient in this proper attitude. The other medical settings referred to above, however, lack such GYN tables, or at least convenient immediate access to such tables.

For example, a typical hospital emergency room has an average of ten examination tables for non-gynecological examinations and one additional table, usually in an enclosed area, for all gynecological and obstetrical examinations. Although the percentage of obstetrical and gynecological patients visiting an emergency room is not high, occasions arise when there may be up to a three-hour wait for access to the gynecological examination room. There is, therefore, a great need for an alternative way of performing gynecological examinations and other emergency room gynecological procedures using the regular emergency room examination table.

A similar need exists in most hospital labor and delivery rooms. Thus, unlike the beds in a hospital ward, so-called labor beds, that is beds occupied by women in labor, are specially designed to be wheeled in and out of the labor room with ease and are equipped with means for elevating the patient's head and knees, as appropriate during labor and delivery. However, this type of bed is very inadequate for many normal gynecological procedures, such as speculum examination or obtaining a blood sample from the fetal scalp. In the past, this deficiency of the labor bed has been overcome by using an inverted bedpan as a pelvic support for positioning the patient in the proper position for examination. Obviously, this solution is totally inadequate.

Moreover, because of this unsuitability of a standard hospital bed for gynecological examinations, a patient who requires a complete gynecological examination often has to be transferred from the patient's room to a special gynecological examination room and then back to the patient's room. This transfer involves moving the patient from her bed to a gurney, then from the gurney to the gynecological examination table, and finally from the examination table back to the gurney and finally from the gurney back to the patient's bed. If the patient is strong enough, a wheelchair may be employed to transfer her between her bed and the examination table. In either event, the transfer requires a nurse and at least one attendant. It is recognized, however, that if a proper hip lifter or pelvic support were available, many of these examinations could be performed in the patient's own bed, thus eliminating the time, labor, and often trauma associated with the transfer procedure.

Another medical setting which presents a problem with regard to gynecological examinations is the doctor's office. Thus, except for the offices of obstetricians and gynecologists, most doctors' offices in this country have only regular non-gynecological examination tables. The reason for this is that such doctors seldom see gynecological patients and, more importantly, gynecological examination tables cost several hundred dollars more than regular examination tables. As a result, when a patient requiring a gynecological examination or other gynecological procedure visits such a doctor's office, she is either referred to a gynecologist or must be examined while lying on a stack of towels or on an inverted bedpan.

Finally, there is the problem of conducting gynecological procedures in radiology facilities. In this regard, a gynecological procedure called hystero-salpingography is frequently done in a radiology office setting. In most cases, medical offices of this type are not equipped with a gynecological examination table for positioning the patient in the proper attitude for conducting the procedure. Moreover, the standard inverted bedpan cannot be used as a hip lifter or pelvic support since the pan is constructed of metal and is thus opaque to the X-rays which are utilized in the procedure. As a consequence, towels are used as a means of properly positioning the patient. However, because this particular procedure takes a substantial period of time, patients frequently complain of discomfort caused by the stack of towels which is used.

A variety of body supporting and positioning devices have been devised, of course, for aiding such gynecological examinations and other gynecological procedures. By way of example, devices of this character are disclosed in U.S. Pat. Nos. 784,425; 3,813,091; and 3,532,336. The devices disclosed in these patents, however, and other similar devices which have been devised, are ill-suited to their intended purposes and, as a result, have not been widely accepted.

Accordingly, a definite need exists for an improved hip lifter or body supporting and positioning device for the purposes described.

SUMMARY OF THE INVENTION

This invention provides such an improved body supporting and positioning device for aiding gynecological examinations, other gynecological procedures, and other similar medical procedures in general. Simply stated, the improved body support, which is referred to herein as a hip lifter or pelvic support, has a relatively rigid, pillow-like body which is adapted to be placed under the patient's buttocks. The pelvic support includes a forward inclined ramp portion and a rear elevated concave platform surface extending rearwardly from the upper edge of the ramp portion. The forward ramp portion facilitates insertion of the support under the patient while in a prone position and, when in place, supports the patient's lower back. The elevated concave platform surface receives and supports the patient's buttocks.

In its preferred configuration, the concave platform surface of the pelvic support has a pair of cavities situated at opposite sides of a vertical longitudinal medial plane of the support and separated by an intervening tapered ridge in the plane. These cavities and intervening ridge conform closely to the posterior buttock portion of the human anatomy.

The body of the pelvic support is an edge wall extending downwardly from the edges of the ramp and platform surface of the support. This edge wall includes a rear portion extending across the rear end of the support and downwardly from the rear edge of the platform surface. According to a preferred feature of the invention, this rear wall portion has a rearwardly facing indentation or recess at the longitudinal medial plane of the support to provide clearance for a speculum or other medical instrument required in the gynecological examination or other medical procedure which is performed with the aid of the support.

The pelvic support or hip lifter of the invention is configured and sized to support the pelvic portion of a patient in an optimum position for examination. The body of the support may be constructed of a material transparent to X-rays so as to permit use of the support in medical procedures requiring X-ray examination through the support. Also, while the support may conceivably be solid, it preferably has a lightweight thin-walled shell or inverted pan-like construction which may be conveniently fabricated by plastic or metal-forming operations, handled, and stacked.

BRIEF DESCRIPTION OF THE DRAWINGS

FIG. 1 is a perspective view of a hip lifter or pelvic support according to the invention;

FIG. 2 is a side elevation of the support illustrating in broken lines a patient positioned on the support;

FIG. 3 is an enlarged section taken on line 3—3 in FIG. 1;

FIG. 4 is an enlarged section taken on line 4—4 in FIG. 1;

FIG. 5 is a top plan view of the pelvic support.

DESCRIPTION OF THE PREFERRED EMBODIMENT

Referring now in detail to these drawings, the illustrated hip lifter or pelvic support 10 of the invention has a relatively rigid pillow-like body adapted to be placed under the patient's lower back and pelvic portion in the manner illustrated in FIG. 2. In its preferred configuration, illustrated, the pelvic support has a hollow, relatively thin-walled inverted pan-like configuration which adapts the support for convenient fabrication from plastic or metal by injection molding or metal-forming operation. In addition, this hollow shell or pan-like configuration permits the support to be easily handled and stacked when not in use.

Pelvic support 10 has a forward inclined ramp portion 12 which serves two purposes. First, it facilitates insertion of the support under a patient while in a prone position. Secondly, when the pelvic support is in position, the ramp portion supports the patient's lower back portion, as shown in FIG. 2.

Extending rearwardly from the rear upper edge of the ramp portion 12 is an elevated concave platform surface 14 for receiving and supporting the patient's buttocks. As shown best in FIG. 1, this platform surface preferably defines a pair of rounded cavities 16 which are situated at opposite sides of the longitudinal vertical medial plane of the support and are separated by an intervening tapered ridge 18 located in the plane. These cavities and the intervening ridge are shaped to conform closely to the posterior buttock region of the human anatomy.

Extending circumferentially about the pelvic support 10 and downwardly from the edges of the ramp 12 and platform surface 14 is an edge wall 20. This edge wall has a rear portion 22 which extends across the rear end of the support and has a rearwardly facing indentation or recess 24 located in the medial plane of the support to provide clearance for a speculum 26 or other instrument which may be required in the medical procedure to be performed with the aid of the support. The lower edge portion of the edge wall 20 is an outwardly directed flange 28 to provide a base surface for the support.

Referring now to FIG. 2, it will be seen that the hip lifter or pelvic support 10 of the invention, when properly positioned under a patient, supports the patient's lower back and pelvic portion in an optimum position for gynecological examination or other gynecological procedures. Support may be used on a conventional examination table or hospital bed and hence may be employed in the various medical settings discussed earlier, thus permitting gynecological examinations and other procedures to be carried out in these various settings with comfort and without the earlier discussed problems and difficulties which are normally encountered in these settings.

The inventor claims:

1. A pelvic support for supporting and positioning the pelvic portion of a patient in an elevated position for examination and other medical procedures, comprising:

a relatively rigid pillow-like body having a forward inclined ramp portion which facilitates placement of the support under the patient while in a prone position and supports the patient's lower back, and an elevated concave generally horizontal platform surface extending rearwardly from the upper rear edge of said ramp portion and configurated and sized for receiving and supporting the patient's buttocks.

2. The pelvic support of claim 1, wherein:

said platform surface defines a pair of cavities situated at opposite sides of the longitudinal vertical medial plane of the support separated by an intervening tapered ridge in the plane, said cavities and ridge conforming closely to the buttock region of the human anatomy.

3. A pelvic support for supporting and positioning the pelvic portion of a patient in an elevated position for examination and other medical procedures, comprising:

a relatively rigid pillow-like body having a forward inclined ramp portion which facilitates placement of the support under the patient while in a prone position and supports the patient's lower back, and an elevated concave platform surface extending rearwardly from the upper rear edge of said ramp portion for receiving and supporting the patient's buttocks, said platform surface defining a pair of cavities situated at opposite sides of the longitudinal vertical medial plane of the support separated by an intervening tapered ridge in the plane, said cavities and ridge conforming closely to the buttock region of the human anatomy, said support having an edge wall about the support including a rear wall portion extending across the rear end of the support and downwardly from the rear edge of said platform surface, said rear wall portion having a rearwardly facing indentation in said plane to provide clearance for a medical instrument used in the medical procedure which is performed with the aid of the support.

4. A pelvic support for supporting and positioning the pelvic portion of a patient in an elevated position for examination and other medical procedures, comprising:

a relatively rigid pillow-like body having a forward inclined ramp portion which facilitates placement of the support under the patient while in a prone position and supports the patient's lower back, and an elevated concave platform surface extending rearwardly from the upper rear edge of said ramp portion for receiving and supporting the patient's buttocks, said support having an edge wall about the support including a rear wall portion extending across the rear end of the support and downwardly from the rear edge of said platform surface, said rear wall portion having a rearwardly facing indentation in said plane to provide clearance for a medical instrument used in the medical procedure which is performed with the aid of the support.

5. The pelvic support of claim 1, wherein:
said support has a hollow thin-walled shell-like body.
6. The pelvic support of claim 5, wherein:
said support has an open bottom whereby a number of said supports may be stacked.
7. The pelvic support of claim 3, wherein:
said support has a hollow thin-walled shell-like body.
8. The pelvic support of claim 7, wherein:
said support has an open bottom whereby a number of said supports may be stacked.
9. The pelvic support of claim 1, wherein:
said support is relatively transparent to X-rays.
10. The pelvic support of claim 5, wherein:
said support is relatively transparent to X-rays.

* * * * *